United States Patent
Osipova et al.

(10) Patent No.: US 8,414,878 B2
(45) Date of Patent: Apr. 9, 2013

(54) **IRILIS BIOPREPARATION BASED ON BACILLUS-STRAIN BACTERIA, *BACILLUS SUBTILIS* AND *BACILLUS LICHENIFORMIS* CONTAINED THEREIN**

(76) Inventors: Irina Grigorievna Osipova, Moscow (RU); Irina Borisovna Sorokulova, Kiev (UA); Elena Aleksandrovna Vasilieva, Moscow (RU); Sergei Gennadievich Trofimov, Chelyabinsk (RU); Vera Franzevna Evlashkina, Moscow (RU); Elena Yurievna Haritonova, Moscow (RU); Sergei Eduardovich Sarkisov, Moscow (RU); Natalia Vasilievna Tereshkina, Moscow (RU); Yurii Igorevich Ostroumov, Moscow (RU); Aleksandr Nikolaevich Doronin, Ekateriaburg (RU); Marina Aleksandrovna Kulichizkaya, Nizhny Novgorod (RU); Aleksandr Aleksandrovich Matveev, Moscow (RU)

( * ) Notice: Subject to any disclaimer, the term of this patent is extended or adjusted under 35 U.S.C. 154(b) by 0 days.

(21) Appl. No.: 11/919,356

(22) PCT Filed: Apr. 28, 2005
(Under 37 CFR 1.47)

(86) PCT No.: PCT/RU2005/000231
§ 371 (c)(1),
(2), (4) Date: Dec. 8, 2009

(87) PCT Pub. No.: WO2006/115430
PCT Pub. Date: Nov. 2, 2006

(65) Prior Publication Data
US 2011/0142924 A1    Jun. 16, 2011

(51) Int. Cl.
| A01N 63/00 | (2006.01) |
| A01N 65/00 | (2009.01) |
| A61K 39/02 | (2006.01) |
| A61K 39/07 | (2006.01) |
| C12N 1/00 | (2006.01) |

(52) U.S. Cl.
USPC . 424/93.1; 424/93.4; 424/93.46; 424/93.462; 424/200.1; 424/234.1; 424/246.1; 435/243; 435/252.31; 435/252.5; 435/325; 435/485; 514/2.4

(58) Field of Classification Search .................. None
See application file for complete search history.

(56) References Cited

U.S. PATENT DOCUMENTS
6,723,326 B1 * 4/2004 Farmer .................... 424/246.1

FOREIGN PATENT DOCUMENTS
| RU | 2 130 316 C1 | 5/1999 |
| RU | 2 131 258 C1 | 6/1999 |
| RU | 2 132 196 C1 | 6/1999 |
| RU | 2 142 287 C1 | 12/1999 |
| RU | 2 158 134 C1 | 9/2000 |
| RU | 2 159 625 C1 | 11/2000 |
| RU | 2 180 575 C2 | 3/2002 |
| RU | 2 182 009 C1 | 5/2002 |
| RU | 2 184 774 C1 | 7/2002 |
| RU | 2 219 238 C1 | 12/2003 |
| RU | 2003 137 794 A | 10/2005 |
| RU | 2 264 454 C2 | 11/2005 |
| SU | 1 722 502 A1 | 3/1992 |
| WO | WO 2005/019417 * | 3/2005 |

OTHER PUBLICATIONS

Osipova et al. Vestn Ross Akad Med Nauk. 2005:(12): 36-40. English Abstract.*
Osipova et al., (Vestnik Rossiiskoi akademii meditsinskikh nauk Rossiiskaia akademiia meditsinskikh nauk (May 2005, available online Apr. 2005) Issue:12, pp. 36-40)).*
Smirnov, V.V. et al., Questions for discussion of creation and application of bacterial preparations for micro flora correction of homoiothermal animals, Microbiological Journal, 1992, vol. 54, p. 82-93.

* cited by examiner

Primary Examiner — Ja'na Hines
(74) Attorney, Agent, or Firm — Pauley Petersen & Erickson

(57) ABSTRACT

A bioengineering, in particular to develop novel probiotic preparations based on *Bacillus*-strain bacteria, which can be used for preventing and treating infectious diseases and disbiosis of a human being, farm animals and birds. The novel strains of *B. subtilis* 07 (VKPM No. B-8611) and *B. licheniformis* 09 (VKPM No. B-8610) exhibit a broad spectrum of antagonistic activity, high proteolytic and amylase activity and a distinct ability in terms of a lysozim production. Such strains do not compete with each other but enter into synergistic relations in the form of an increased antagonistic action of the biopreparation. The inventive biopreparation comprises the *B. subtilis* 07 VKPM No. B-8611 and *B. licheniformis* 09 VKPM No. B-8610 strains and a protective medium. Such biopreparation can also contain a solvent and/or filler and exhibits an increased antagonistic activity with respect to a wide range of pathogenic and opportunistic pathogenic microorganisms and a resistance to quite a number of antibiotics.

20 Claims, No Drawings

IRILIS BIOPREPARATION BASED ON BACILLUS-STRAIN BACTERIA, *BACILLUS SUBTILIS* AND *BACILLUS LICHENIFORMIS* CONTAINED THEREIN

CROSS REFERENCE TO RELATED APPLICATION

This application is a U.S. National Phase entry of PCT International Patent Application PCT/RU2005/000231, filed on 28 Apr. 2005.

BACKGROUND OF THE INVENTION

1. Field of the Invention

This invention relates to biotechnology and the creation of new probiotic preparations based on *Bacillus*-strain bacteria that can be used as prophylaxis and treatment of infectious diseases and dysbiosis of different origin of human, farm livestock and poultry.

2. Discussion of Related Art

Biopreparations based on *Bacillus*-strain bacteria are well-known. Biopreparations: probiotics based on *Bacillus*-strain bacteria contain strains possessing various spectrum of antibacterial and antifungal activity. The effectiveness of these preparations is determined by the width of spectrum and its antibacterial activity contained in strains preparation.

The probiotic Bactisubtil ("Marion Merrell" Company/France/) and its analogue Flonivin ("Galenika" Company/Yugoslavia/) are wide spread in medical practice in the West Europe countries. They contain the culture of strain *B. cereus* IP 5832 (collection of Institute Pasteur (Paris)). Well-known Vietnamese preparation Biosubtyl contains the strain *B. subtilis* as an active component.

The base of Enterogermina ("Sanofi Winthrop" Company, Italy) is the culture *B. clausii*.

The biopreparation Cereobiogen ("Xing Lap" Company, China) is also well-known. The effective agent of it is *B. cereus* DM-423 (V. V. Smirnov, S. R. Reznik, I. B. Sorokulova, V. A. Vyunitskaya. Questions for discussion of creation and application of bacterial preparations for micro flora correction of homoiothermal animals: Microbiological Journal, 1992, volume 54, N->6, p. 82-93).

One disadvantage of these probiotic preparations is the restricted spectrum of treatment activity as they are aimed against a small group of pathogenic bacteria.

Medical preventive biopreparation Bactisporin for treatment of broad spectrum of diseases, containing lyophilized biomass of the strain Bacillus subtilis 3H and protective media on the base of saccharose-gelatine formula and lactose (Patent RU N° 2130316, A61K 35/66, published on 20.05.1999).

However, the biopreparation Bactisporin is not efficient against a set of acute enteropathogenic bacteria, for example, caused by the bacteria of stem *Pseudomonas* spp., *Streptococcus* spp., *Enterococcus* spp.

Biopharmaceutical preparation Deprecan A, containing recombinant strain of *Bacillus subtilis* is well-known and produces α-2-interferon of the human, strain *Bacillus licheniformis* and an excipient. The preparation can contain recombinant strain of *Bacillus subtilis* BKPM (БКПМ) No.-7289. The preparation has antibacterial, antiviral and immunomodulatory activity and can be used while treating various diseases of infectious and noninfectious nature (Patent RU No. 2158134, A61K 35/74, published on 20.09.2000).

However, Deprecan A contains recombinant strain of plasmid, determining resistance to kanamycin, but this does not meet the requirements of World Health Organization.

A well-known preparation Biosporin is used prophylaxis and the treatment of gastrointestinal diseases of human, and contains the vital cells of strains *Bacillus subtilis* 3 (VKPM (ВКПМ, "All-Russian Collection of Industrial Microorganisms") No. B-2335) and *Bacilllus licheniformis* 31 (VKPM, No. B-2336) and a vehicle (Patent SU No. 1722502, A61K 35/74, published on 30.03.1992).

Biosporin is characterized by the high antagonistic activity to the wide spectrum of pathogenic and opportunistic microorganisms (Sorokulova I. B., 1997).

One disadvantage of Biosporin is that strains contained are susceptible to antibiotics. Therefore this preparation is not recommended to be used together with antibiotics when treating.

The closest analogue is the preparation against viral and bacterial infections, containing the mixture of biomass of strain *Bacillus subtilis* BKPM No. B-7092, *Bacillus subtilis* BKPM No. B-7048, *Bacillus licheniformis* BKPM No. B-7038 in its spore form with the titre of not less than $3 \times 10^{10}$ spore/g, and stabilizer, that is, starch and sucrose. (Patent RU No. 2142287, A61K 35/74, published on 10.12.1999).

One disadvantage of the well-known preparation is the use of the recombinant strain, containing plasmid, determining resistance to antibiotics.

Among the preparations of veterinary application strain Bacillus subtilis X-15 is known and is used for prophylaxis and treatment of cow's endometritis (Patent RU No. 2180575, C12N 1/20, published on 20.03.2002).

One disadvantage of the preparation on the base of stain Bacillus subtilis X-15 is the restricted action spectrum as it is active against a small group of microorganisms, causing the cow's endometritis.

A probiotic preparation Subtilis is also known and is based on liquid or lyophilized freeze-dried strain culture *Bacillus subtilis* VKM No. B-2250 D. This preparation is designed for prevention and treatment of gastrointestinal diseases of animals, birds and fish, and it increases the feed absorbency and increases producing capacity and weight gain (Patent RU No. 2184774, C12N 1/20, published on 10.07.2002).

One disadvantage of the preparation Subtilis is its restricted spectrum of antagonistic activity.

The closest analogue is the probiotic preparation of compound action, containing the following components, vol. %: mixture of biomass Bacillus subtilis VKPM No. 4759 with the titer $1 \times 10^7 - 1 \times 10^9$ of live microbial cells and biomass *Bacillus licheniformis* 2336/105 with the titer $1 \times 10^8 - 10 \times 10$ of live microbial cells in 1 ml of normal saline 92 to 98%, and stabilizer based on serum of the cattle's blood or milk or its mixture, sucrose and gelatin of 2 to 8%. The preparation possesses antibacterial and antiviral activities and is capable for prolonged synthesis of interferon in various parts of open body cavities. (Patent RU No. 2159625, A61K 35/66, published on 27.11.2000)

SUMMARY OF THE INVENTION

One object of this invention is to obtain new strains of Bacillus subtilis and *Bacillus licheniformis* and the development of probiotic preparation based on the strains. This preparation includes expressed antagonistic activity concerning the opportunistic microorganisms due to the high lysozyme, proteolytic and amylase activities, contained in the biopreparation of strains. It is very convenient to practice and has prescription forms.

This invention can increase efficiency of prophylaxis and treatment of different infectious diseases and dysbiosis due to the enlargement of spectrum of antagonistic activity of the bacteria strains contained in biopreparation Irilis, and can increase resistance of biopreparation to the enzymes of the gastrointestinal tract and application facility.

According to this invention, new strains *Bacillus subtilis* 07 (VKPM No. B-8611) and *Bacillus licheniformis* 09 (VKPM No. B-8610) contained in the biopreparation Irilis, have the wide spectrum of antagonistic activity, high proteolytic and amylase activity (*B. subtilis* 07) and expressed ability to secrete of (*B. licheniformis* 09). They do not compete with each other and start synergistic relations and this is expressed in the increase of antagonistic action of the biopreparation.

Strain *B. subtilis* 07 (VKPM No. B-8611) has been deposited in the Russian National Collection of Industrial Microorganisms (VKPM), having an address of 1 Dorozhnyi Proezd, Moscow, 113545, Russia, on 29 Aug. 2003 (converted to a deposit under the Budapest Treaty on 6 Aug. 2004). Strain *B. licheniformis* 09 (VKPM No. B-8610) has been deposited in the Russian National Collection of Industrial Microorganisms (VKPM), having an address of 1 Dorozhnyi Proezd, Moscow, 113545, Russia, on 29 Aug. 2003 (converted to a deposit under the Budapest Treaty on 6 Aug. 2004). Strains *B. subtilis* 07 (VKPM No. B-8611) and *B. licheniformis* 09 (VKPM No. B-8610) are extracted form the healthy wheat and include the following properties.

*Bacillus subtilis* VKPM No. B-8611 are gram-positive bacteria, they are aerobic spore-forming rod bacterium, size 2.7–0.6×0.8-0.7 µm, located separately or in the form of chains. Cells are motile. In an aerobic environment they form spores of oval shape that are placed in the center of the cell. While sporogenesis of a cell they are not swelling.

In medium Gauze No. 2, wort agar, medium Gromiko the strain has abundant growth, and forms dull rough colonies of the flesh color with scalloped margins. They can be easily picked out by the loop from the agar.

In protoplasm of bacterial cells of the strain after the growth in glucose agar media the inclusions of poly-r-hydroxy-butyric are not detected. On beef-extract broth the culture forms the film.

It does not grow in anaerobic environment, it does not hydrolyze urea, and it does not form gas from the nitrates in anaerobic environment, and it does not produce arginine dihydrolase. The culture forms the catalase. It gives positive reaction Foges Proscauer, and it grows in 7% NaCl. It hydrolyses starch and casein and it liquefies gelatin. It ferments glucose, gum sugar, wood sugar, mannitol with the formation of the acid without gas. It reduces the nitrates to nitrites, it bleaches methylene blue. It possesses coagulated and lecithinezed activity, and possesses high proteolytic and amylase activity.

Main physical and biochemical properties of *B. subtilis* VKPM No. B-8611 are shown in Table 1 and Table 2.

*B. licheniformis* VKPM No. B-8610 are gram-positive spore-forming bacillus, having a size of 2.6–0.7×0.5-0.6 µm. Cells are motile, peritrichia are located mostly in the form of chains. Spores are of oval form, and are located in the center of the cell. The cells during sporogenesis are not swelling. After the growth in glucose agar in protoplasm the inclusions of poly-r-hydroxy-butyric are not detected.

On beef-extract agar media it forms the colonies with dull rough surface, non-transparent, tightly attached to the agar: quite often there is slime on the surface. On beef-extract broth the re is a wrinkled film, sometimes with cream colored tint.

Culture forms catalase, and it includes the ability to grow on agar in an anaerobic environment. It gives positive reaction Foges Proscauer, and it grows at 7% NaCl. It hydrolyses starch and caseine, but it does not hydrolyse urea. Gelatin liquefies slowly. It ferments glucose, gum sugar, wood sugar, mannitol with the formation of the acid without gas. It reduces the nitrates to nitrites; in anaerobic environment it forms gas from the nitrates. It produces arginine dihydrolase, lysozyme. It does not possess coagulated and lecithinezed activity.

Main properties of strain *B. licheniformis* VKPM No. B-8610 are shown in Table 1 and Table 2.

Strains *B. subtilis* VKPM No. B-8611 and *B. licheniformis* VKPM No. B-8610 have high antagonistic activity concerning the wide spectrum of pathogenic and opportunistic microorganisms and resistance to a number of antibiotics.

In the content of this preparation Irilis the mentioned strains can be used in different combinations, for example, in equal ratios (of titers of cells): the biomass of the strain *B. subtillis* VKPM No. B-8611 in the titer $1\times10^9$ KFU/ml and the biomass of the strain *B. licheniformis* VKPM No. B-8610 in the titer $1\times10^9$ KFU/ml or in any other ratio in the limits of (1-100):(100-1). For example, the biomass of the strain *B. subtilis* VKPM No. B-8611 in the titer $5\times10^9$ KFU/ml and the biomass of the strain *B. licheniformis* VKPM No. B-8610 in the titer $1\times10^9$ KFU/ml, or the biomass of the strain *B. subtilis* VKPM No. B-8611 in the titer $1\times10^{10}$ KFU/ml and the biomass of the strain *B. licheniformis* VKPM No. B-8610 in the titer $5\times10^9$ KFU/ml, or the biomass of the strain *B. subtilis* VKPM No. B-8611 in the titer $1\times10^9$ KFU/ml and the biomass of the strain *B. licheniformis* VKPM No. B-8610 in the titer $1\times10^7$ KFU/ml, etc.

The biopreparation Irilis contains also the safety medium to provide the viability of bacteria during technological processing, obtaining final prescribed form and further storage. As a safety medium it can contain, for example, sucrose-gelatin medium, dried milk, gelatine, lactose, saccharose, etc.

The biopreparation Irilis can additionally contain definite solvent. As the definite solvent, distilled water or boiled water, normal saline can be used and so on.

The biopreparation Irilis can additionally contain bulking agent applied usually while producing various prescribed forms. When forming pills it can contain, for example, dextrans, polyglucin, starch, polyvinylpyrrolidone, saccharose, lactose, calcium stearate, glucose, sodium bicarbonate, aluminum hydrate, methylcellulose, talcum, etc. While obtaining suppository or candles as excipient it contains, for example, cooking fat, paraffin, lanolin, cocoa butter, gel of aluminum hydrate, etc.

The biopreparation can be encapsulated and immobilized on any type of carriers or adsorbents, for example, on aerosil, cellulose, activated charcoal, carboxymethyl cellulose, hydroxyethyl cellulose, chitosan, etc.

The biopreparation can also be lyophilizated.

The biopreparation Irilis can be used for per oral or vaginal or rectal or external usage in the form of an aqueous suspension. Mechanism of action of the biopreparation Irilis is based on adhesive and antagonistic activity of bacteria—probiotic, producing various physiologically active substances and displacing pathogenic and opportunistic microorganisms from the digestive tract of microorganism and stimulating specific and non-specific defense reactions of microorganism.

DETAILED DESCRIPTION OF THE INVENTION

This invention is illustrated by the following examples.

Example 1

Production of a Liquid Preparation

Strains are cultivated separately or on solid media or nutrient broths.

In laboratory stationary technology the cultivation of strains is carried out in solid agar media in mattresses or in glass bottles on a labor rocker or a shaker at the temperature from 22 to 38° C. during from 12-16 hours to 7 days. On completion of incubation, the biomass grown on the surface of the nutrient medium is rinsed off by the stabilizer, containing 5% lactose solution, it is combined in proportions 10:1, and then they are bottled. The biopreparation with the content of biomass of the strain *B. subtilis* VKPM No. B-8611 in the titer $1\times10^1$ KFU/ml and biomass of the strain *B. licheniformis* VKPM No. B-8610 – $1\times10^9$ KFU/ml is received.

In industrial technology the cultivation of strains is carried out on reactor/cultivator with the nutrient medium for cultivation at the temperature 35-38° C. during 10-18 hours. The process is considered to be completed if the concentration of cells is 4-5 bln/ml and the ratio of spores and vegetative cells is 1:1. On completion of incubation the separately grown bacterial cultures are mixed together in proportion of 1:1. Saccharose gelatin safety medium is added and then bottle this mixture. The biopreparation with biomass of the strain *B. subtilis* VKPM No. B-8611 in the titer $5\times10^9$ KFU/ml and the biomass of the strain *B. licheniformis* VKPM No. B-8610– $5\times10^9$ KFU/ml is produced.

Example 2

Production of the Preparation in the Form of Lyophilizate

In laboratory stationary technology the cultivation of strains is carried out in solid agar media in mattresses or in glass bottles on a labor rocker or a shaker at the temperature from 22 to 38° C. during from 12-16 hours to 7 days. On completion of incubation the biomass grown on the surface of the nutrient medium is rinsed off by the safety medium containing 10% glycerol solution, is bottled into the ampoules (vials) or into the stainless cassettes and then is frozen and dehydrated in the lyophilized vacuum freeze device or is dried by spray-type freeze device.

In industrial technology the cultivation of strains is carried out on reactor/cultivator with the nutrient medium for cultivation at the temperature 35-38° C. during 10-18 hours. The process is considered to be completed if the concentration of cells is 4-5 bln/ml and the ratio of spores and vegetative cells is 1:1. On completion of incubation, the separately grown bacterial cultures are mixed together in proportion of 2:1. Stabilizer is added and the mixture is bottled into the ampoules (vials) or into the stainless cassettes and then is frozen and dehydrated in the lyophilized vacuum freeze device or is dried by spray-type freeze device.

Example 3

Production of the Preparation in the Pill Form is Possible

Grown cultures of the strains *B. subtilis* VKPM No. B-8611 and *B. licheniformis* VKPM No. B-8610 after adding components of suspended media are dehydrated in lyophilized vacuum freeze device or in spray-type freeze device, then it is combined with granulated material, lubricants (starch or calcium stearate) and is pressed on rotary presses.

10 experimental and industrial series of pill form of the preparation has been studied for stability. As the results show, directly after pressing the content of the live *B. subtilis* VKPM No. B-8611 and *B. licheniformis* VKPM No. B-8610 in the pills is not less than $10^{9\text{-}7}\text{-}10^{8\text{-}6}$ KFU/dose (correspondingly). After storing the pills for 12 months the content of the live microbial cells in all lots has not been less $10^{9\text{-}7}\text{-}10^{8\text{-}6}$ KFU/dose.

Example 4

Production of the Preparation in the Form of Suppositories is Possible

Grown cultures of the strains *B. subtilis* VKPM No. B-8611 and *B. licheniformis* VKPM No. B-8610 after adding components of slurrying medium are dehydrated in lyophilized vacuum freeze device or in spray-type freeze device, and are mixed with a bulking agent (cooking fat or paraffin) and are produced the suppositories by a special device.

10 experimental and industrial series of the preparation has been studied for stability.

As the results show, directly after pressing the content of the live *B. subtilis* VKPM No. B-8611 and *B. licheniformis* VKPM No. B-8610 in the suppositories is not less than $10^{9\text{-}7}\text{-}10^{8\text{-}6}$ KFU/suppository (correspondingly). After storing the pills for 12 months, the content of the live microbial cells in all lots has not been less $10^{9\text{-}7}\text{-}10^{8\text{-}6}$ KFU/suppository.

Example 5

All variants and forms of the biopreparation Irilis according to the Examples 1 or 2 or 3 or 4 are tested for harmlessness on laboratory animals, specific antagonistic activity to test cultures, representatives of various groups of pathogenic and opportunistic microorganisms and resistance to antibiotics.

The biopreparation Irilis has harmlessness characteristics.

To determine the harmlessness, the content of the bottle is dissolved in 0.5 ml of normal saline and introduce it to the mice orally. For every variant, they use 10 mice, at a weight of 15-16 g. The preparation is considered harmless if all mice stay alive during 5 days of observation and disease was not detected in any mouse.

The biopreparation Irilis includes the wised spectrum of antagonistic activity regarding the test-strains of cultures of pathogenic and opportunistic microorganisms. In Table 3, you can see characteristics of antagonistic activity of the preparation regarding pathogenic and opportunistic microorganisms, defined at various infectious diseases and dysbiosis of diverse aetiology. To determine the special activity, the antagonuistic activity of the variants of the preparation are studied regarding the clinical test-cultures. The examination is carried out by method of deferred antagonism. For this, the content of the bottle is dissolved in 1 ml of normal saline. The received suspension is plated along the Petri dish with agar medium Gauze #2. Plating is incubated in the thermostat at 37° C. during 72 hours. Then to the grown culture test-microorganisms are streak plated (5000 mln suspensions of diurnal cultures in the normal saline). The results are checked 18 hours later after incubation at 37° C. by the size of growth absence of test-cultures.

Growth control of test-cultures is the parallel growth of them in plates with agar medium Gauze #2 without studied culture.

Data from the Table 3 show that the optimal quantity of the alive cells in one dose of the preparation is $1\text{-}5\times10^9$. The further increase of the microbe cells will not change significantly the antagonistic activity of the preparations regarding the test-cultures of microorganisms.

Example 6

To determine the therapeutical effect of the probiotic Irilis received according to the Examples 1 or 2 or 3 in comparison with the application of the preparation Pectosorbin, in the farm, piglets with long-term bad gastrointestinal diseases with the symptom complex of diarrhea form 3 groups of piglets of 1-2 days age with clinical sign of dyspepsia (diarrhea, liquefied stool, dejecture had sour smell, contained the gas bubbles, loss of appetite, dryness and paleness of the mucous tunics, rapid pulse, muffled heart sounds, tachypnoe).

After clinical examination it was determined that 69 piglets have trivial dyspepsia, and 12 piglets have toxical dyspepsia.

While conducting the bacteriological study of the samples of piglets' faeces in all ill piglets the pathogenic *Escherichia*

($10^8$-$10^{11}$ bacteria in 1 g) are detected in large quantities, whereas the *Escherichia* strains of the normal representatives of the large intestine can be detected only at 8 piglets ($10^3$-$10^4$ bacteria in 1 g).

Pathogenic *Escherichia* in contrast to the normal representatives of the intestine, as a rule, does not ferment the lactose and cause the death of the mice while intraperitoneal introduction. While serotyping the detected strains of the pigs, 11 strains belong to the enteropathogenic serogroup 0141; the remaining 40 strains did not agglutinate by the type specific serum. The results of the study show the disorder of the micro flora of the large intestine of the ill piglets with dyspepsia (dysbacteriosis) that is the cause of their disease.

The piglets of the first and the second group after 3-4 hours of water-starvation diet 20-30 minutes before the feeding are given Irilis in the amount of 2 and 4 doses respectively 2 times a day with the interval of 12 hours before the clinical recovery. The piglets of the third group three times a day before clinical recovery take Pectosorbin with colostrums in the dose of 0.26 g for every kilo of live weight according to the instruction for use. The piglets are observed clinically taking into account the number of recovered piglets and the duration of treatment. The recovery is detected by the absence of diarrhea signs, pathological additives in faeces, meteorism (tympanism), spasms, improvement of general condition, appetite. The results are shown in Table 4.

As shown in Table 4, probiotic Irilis provides high effectiveness while applying it in the amount of 4 doses 2 times a day. The recovery comes after 4 to 6 times of applying Irilis while following the diet. Normalization of gut organisms eliminates the dehydratation and this excludes the necessity of rehydration measures. After cancellation of the preparation the disease is not detected.

Example 7

To determine the efficiency of the preparation Irilis when treating the calves with symptom complex of diarrhea and the evaluation of its prophylactic action on the animals up to 2 months age, three groups of 100 healthy newborn calves of 1 to 2 days old, were formed. The weight of calves at birth is 28 to 30 kilos.

The calves of all groups were fed according to the recommendations of growing procedure: 1.5 to 2 liters of colostrums (milk) during every feeding three times a day. For the first time the colostrums is given not later than after 1.5 hours after birth. The calves of the first two groups (40 animals each) are given the preparation 20 to 30 minutes before the second feeding during five days by two courses with the interval of 3 to 4 days: the preparation Irilis is given of 1 and 2 doses correspondingly. Before giving the preparation, the content of one ampoule (bottle) is dissolved in 0.100 ml of water boiled and then cooled to the temperature of 38-39° C. The calves of the first group are given 50 ml, the calves of the second test group are given 100 ml of the preparation. The third group is a control group (20 animals) and it is not given the preparation Irilis.

The calves are weighted at birth and at the age of 2 months. Every day their physical condition, appetite and the functioning of their digestive system (type of feces, meteorism), and behavior of an animal are observed. At the end of experience, five calves of every group are taken blood tests for hematomancy. With a Sahli hemoglobinometer the hemoglobin in their blood is detected, with a Gorjaev's chamber the blood cells are detected, with a general method their leukogram is determined, and the concentration of the whole protein in blood serum is defined refractometrically. The content of immunoglobulins is detected by a zinc sulphate test, and the content of lisolim is defined according to E. V. Ermolaeva, germicidal activity determined according to S. V. Smirnova and T. A. Kuzmina. The results of the study are shown in the Table 5.

As shown in the Table 5, application of the probiotic Irilis does not influence significantly the concentration of hemoglobin in the blood, the number of blood corpuscles and leukogram. Moreover, in the blood of the calves that were given the preparation the level of whole protein in the blood serum, immunoglobulins, lizopim and serum bactericidal activity increase considerably.

It was determined that Irilis does not influence negatively the health of animals, but it increases greatly their gastrointestinal diseases resistance, improves the quality of their lives, and they do not lose weight. (Table 6)

As shown in the Table 6, in the control group that was not given the preparation 15 calves of 20 got ill, that is 75% of the number of animals in the group, but in the first test group (1 dose of Irilis 1 time a day), 11 calves of 40 (27.5%) got ill and in the second test group (2 doses of Irilis 2 times a days) 7 calves of 40 (17.5%) got ill. Prophylactic efficiency of the probiotic Irilis is 72.5% and 82.5% correspondingly.

The calves of the control group get ill at the $2^{nd}$ and $9^{th}$ day, and the disease is of serious form. As a result the death animals are 30% and the alive animals are 70%. The application of the preparation Irilis in the amount not less than 2 doses is not worthwhile. That is confirmed by the high percents of the alive animals and average daily weight increment of 95% and 9% correspondingly.

Example 8

Application efficiency of the preparation Irilis for prophylactic of gastrointestinal diseases with symptom complex of diarreas is determined on the farm, having long-term unfavorable results of these diseases, in comparison with the preparations pectosorbin and immunoglobulin. 105 new born calves are divided into three groups of 35 animals each. All animals are healthy, normally developed and the difference among the groups of the average live weight does not exceed 2%.

The calves of the first group are given the preparation Irilis (2 doses) 20 to 30 minutes before the colostrums. The calves of the second group are given pectosorbin according to the recommendations of its application. The calves of the third group are given unspecific immunoglobulin intramuscularly according to the recommendations of its application.

Prophylactic course of groups is: for the first group—10 days, for the second group—10 days, for the third group—50 days. Observation period is 60 days. Calves are weighed at birth, one month later and at the end of the observation period. Every day a clinical condition is observed, taking attention to the number of ill animals, clinical course and clinical outcome. The results of study are shown in the Table 7.

As shown in the Table 7, the efficiency of the probiotic Irilis in comparison with well-known preparations pectosorbin and immunoglobulin is much higher, that is confirmed by the rates of alive animals and average daily growth of body weight.

Example 9

The tests of introducing the probiotic preparation Irilis into the traditional scheme of feeding in the poultry farming while breeding the broiler chickens are carried out. The chickens are divided into 4 groups, that are given are:

1 g. Of the preparation препарат <<Vetom>> manufactured by NPF-IZ <<Koltsovo>>, 2 g. Of the preparation Irilis 3 g. Of the preparation STF, manufactured by <<Bioavtomatika>> Company Limited, 4 g. Of the preparation <<Enterosporin>>

Experimental prophylactic scheme of day breeding is the following:

1$^{st}$ day—probiotics with feeding
1-3 days—fluoroquinolones
4-13 days—probiotics with feeding.

Further, the prophylactic scheme used on the farms is applied.

Results are registered according to the main technological factors: weight of chickens at 1st, 7th, 14th, 28th, 35th and 42nd days and when taking to slaughtering; calculations of loss of cattle every week and total when taking to slaughtering. The results of study are shown in the Table 8.

Data provided in the Table 8 show that the usage of the preparation Irilis during the process of breeding the chickens provides the high results of livestock survivability. The preparation Irilis influences positively the organism of chickens, providing the big increase of live weight in comparison with the control.

Consequently, the tests carried out of the preparation Irilis have revealed the possibility and high efficiency of its application while growing the livestock and poultry. It provides the inhibition of the pathogenic *Escherihia*, maintenance of the optimal microbial balance in digestive tract, increase of non-specific animal resistance, their safety and growth of body weight, has prophylactic medical effect against the diseases that are followed by the diarrhea and it also a prophylactic remedy from the dysbacteriosis. The advantage of the preparation Irilis is the chromosomal resistance to antibiotics contained in its strains. This makes it possible to apply this preparation in the complex of antimicrobial therapy.

TABLE 1

Cultural, morphological and biochemical properties

| Properties | B. subtilis VKPM No. B-8611 | B. licheniformis VKPM No. B-8610 |
|---|---|---|
| Growth in anaerobic environment | − | + |
| Fermentation of | | |
| glucose | + | + |
| arabinose | + | − |
| wood sugar | + | + |
| mannitol | + | + |
| Utilization of | | |
| citrate | + | + |
| proshunat | − | + |
| Hydrolysis of | | |
| starch | + | + |
| urea | − | − |
| casein | + | + |
| tyrosine | − | − |
| Reduction on nitrates | + | + |
| Gas production from NO$_3$ in anaerobic environment | − | + |
| Bleach of methylene-blue | + | + |
| Argininedehydrolase | − | + |
| Lecithin | − | − |
| Hyaluronidase | − | − |
| Hemolytic activity | − | − |
| Forming of globules of polioxyoil acid on glucose agar | − | − |
| Lysozymic activity | + | + |
| Growth at 50° C. | + | + |
| Growth at 7% NaCl | + | + |

TABLE 1-continued

Cultural, morphological and biochemical properties

| Properties | B. subtilis VKPM No. B-8611 | B. licheniformis VKPM No. B-8610 |
|---|---|---|
| Growth at 65° C. | − | − |
| Production of acid and gas from glucose | − | − |
| Production of acid from glucose | + | + |

TABLE 2

Sensitivity to antibiotics of the strains of the stem *Bacillus*

| | Diameter of delay zones of cultures growth, mm | |
|---|---|---|
| Preparation under study | B. subtilis VKPMB-8611 | B. licheniformis VKPM B-8610 |
| PENICILLIN | | |
| Azlocillin | 19 ± 0.1 | 16 + 0.1 |
| Amoscipillin | 19 ± 0.2 | 16 + 0.1 |
| Ampicillin | 11 ± 0.2 | 0 |
| Carbenicillin | 23 ± 0.5 | 20 + 0.1 |
| Mezlocillin | 21 ± 0.2 | 15 + 0.2 |
| Methicillin | 20 ± 0.1 | 10 ± 0D |
| Oxacillin | 15 ± 0.3 | 11 + 0.1 |
| Benzylpenicillin | 7 ± 0.1 | 3 ± 0.2 |
| Piperacillin | 15 + 03 | 11 + 0.1 |
| Ticarcillin | 25 ± 0.4 | 21 + 0.2 |
| CARBAPENEMS | | |
| Imipenems | 38 ± 0.2 | 30 + 0.1 |
| CEPHALOSPORIN | | |
| Mocsalactam | I ± 0.2 | 12 + 03 |
| Cephalothin | 35 ± 0.1 | 21 + 0.3 |
| Cefazolin | 25 ± 0.2 | 19 + 0.2 |
| Cefamandole | 35 ± 0.3 | 15 + 0.1 |
| Cefoxitin | 18 ± 0.1 | 13 + 0.1 |
| Cefoperazone | 15 ± 0.2 | 13 + 0.1 |
| Cefotaxime | 15 ± 0.1 | 9 + 0.1 |
| Ceftazidime | 6 ± 0.3 | 13 + 02 |
| Ceftizoxime | 3 ± 0.1 | 11 ± 0.1 |
| Ceftriaxone | 20 + 0.4 | 12 + 02 |
| Cefuroxime | 2 ± 0.1 | 3 ± 0.1 |
| AMINOGLYCOSIDE | | |
| Amicacin | 22 ± 0.3 | 17 + 0.2 |
| Gentamicin | 25 ± 0.3 | 19 + 0.2 |
| Kanamycin | 22 ± 0.2 | 21 + 0.1 |
| Tobramycin | 25 ± 0.1 | 20 + 0.2 |
| OTHERS | | |
| Vancomycin | 12 ± 0.1 | 10 ± 0.1 |
| Clindamycin | 9 + 0.2 | 12 + 0.1 |
| Tetracycline | 26 + 0.1 | 24 + 0.1 |
| Chloramphenicol | 18 ± 0.3 | 10 ± 0.1 |
| Polymyxin E | 11 + 0.1 | 10 + 0.2 |
| Nitrofurantoin | 15 + 0.2 | 20 + 0.1 |
| Ttrimethoprim | 23 ± 0.1 | 25 + 0.2 |
| Bakgtrim | 29 ± 0.2 | 31 + 0.3 |
| Norfloxacin | 24 ± 0.2 | 25 + 0.2 |
| Nalidixic acid | 21 ± 0.1 | 15 + 0.1 |

TABLE 3

Antagonistic activity of the variants of the preparation Irilis concerning
the clinical strains of the pathogenic and opportunistic microorganisms.

| | Variants of the biopreparation (ratio $B.\ subtilis:B.\ licheniformis$) × $10^{8\text{"}6}$ KFU/ml Zones of growth delay of the test-strains (mm) | | | | |
|---|---|---|---|---|---|
| Test cultures | 1:1 | 2:1 | 5:1 | 1:10 | 10:1 |
| *Shigella* some (n = 25) (from the patients with dysentery) | 10-12 | 12-15 | 12-15 | 12-15 | 12-15 |
| *Salmonella typhimurium* (n = 25) (from the patients with salmonellosis) | 10-13 | 12-18 | 12-18 | 12-18 | 12-18 |
| *Escherihia coli* 0:157:H7 (n = 13) (from the patients with enterohemorrhagic colitis and form animals) | 9-10 | 11-13 | 11-13 | 11-13 | 11-13 |
| *Staphylococcus aureus* (n = 20) (at dysbacteriosis of intestine) | 10-15 | 15-20 | 15-20 | 15-20 | 18-20 |
| *Staphylococcus aureus* (n = 45) (at pyoinflammatory diseases) | 12-16 | 15-18 | 15-20 | 18-20 | 22-25 |
| *Staphylococcus aureus* (n = 29) (at dysbiosis of vagina) | 15-18 | 15-20 | 18-22 | 18-22 | 20-25 |
| *Proteus vulgaris* (n = 18) (at dysbacteriosis of intestine) | 10-15 | 15-20 | 15-20 | 15-20 | 15-20 |
| *Proteus vulgaris* (n = 18) (from the patients with pyelonephritis) | 10-12 | 12-15 | 12-15 | 12-15 | 12-15 |
| *Proteus mirabilis* (n = 15) (at dysbacteriosis of intestine) | 15-18 | 18-20 | 18-20 | 18-20 | 18-20 |
| *Candida albicans* (n = 42) (at dysbacteriosis of intestine) | 25-30 | 25-30 | 25-30 | 25-30 | 25-30 |
| *Candida albicans* (n = 20) (at dysbiosis of vagina) | 25-30 | 25-30 | 25-30 | 25-30 | 25-30 |
| *Escherihia coli* (n = 18) (from the patients with pyelonephritis) | 20-22 | 22-25 | 22-25 | 22-25 | 22-25 |
| *Escherihia coli* (n = 15) (at pyoinflammatory diseases) | 10-12 | 12-15 | 12-15 | 12-15 | 12-15 |
| *Streptococcus* (n = 17) (at pyoinflammatory diseases) | 10-12 | 12-15 | 12-15 | 12-15 | 12-15 |

TABLE 4

Comparative efficiency of the application of Irilis and
Pectosorbin to treat the gastrointestinal diseases of
the piglets caused by the pathogenic micro flora

| | Group of piglets | | |
|---|---|---|---|
| Rates | First, heads = 27 Irilis 2 doses | Second, heads = 27 Irilis 4 doses | Third, heads = 27 Pectosorbin |
| Recovered, heads. | 24 | 26 | 20 |
| Died and were killed, heads. | 3 | 1 | 7 |
| Course of treatment, days | 4.5 ± 0.4 | 2.0 + 0.6 | 6.5 ± 0.6 |
| Medical efficiency, % | 88.9 | 96.3 | 74.1 |

TABLE 5

Study of the main bloods rates of 2 months old
calves after taking prophylactic measures

| | Groups of calves | | |
|---|---|---|---|
| Rates | Experimental group 1, (heads = 40) | Experimental group 2, (heads = 40) | Control group 3, |
| Hemoglobin, g/l | 127.0 ± 13.6 | 132.7 ± 4.0 | 126.0 ± 3.0 |
| Erythrocytes, | 7.2 + 0.2 | 7.4 ± 0.4 | 7.2 ± 0.2 |
| Leucocytes, | 6.4 ± 1.0 | 6.3 ± 0.9 | 6.8 ± 0.7 |
| Crude protein, g/l | 62Д ± 1.6 | 70.5 ± 1.7 | 61.0 ± 2.6 |
| Immunoglobulin general, g/l | 29.4 ± 1.9 | 38.0 + 2.1 | 27.4 ± 1.7 |
| lysozyme, mcg/k | 770.0 ± 31.0 | 980.0 ± 22.0 | 765.0 + 33.0 |
| Bactericidal activity, % | 67.0 + 0.5 | 86.5 ± 2.0 | 60.2 ± 1.7 |
| Leukogram, %: | | | |
| Basophils | — | — | — |
| Eosinophils | 4 | 3 | 3 |
| Neutrophils: | | | |
| adolescent | — | — | — |
| stab | 3 | 3 | 2 |
| segmented | 25 | 23 | 24 |
| Lymphocytes | 66 | 68 | 69 |
| Monocytes | 2 | 3 | 2 |

TABLE 6

Prophylactic efficiency of Irilis when growing the veal calves

| Rates | Groups of calves | | |
|---|---|---|---|
| | First, heads = 40 | Second, heads = 40 | Third, heads = 20 |
| Got ill. heads. (%) | 11 (27.5) | 7 (17.5) | 15 (75.0) |
| At the age. days | 3.5 ± 0.3 | 3.5 ± Д1 | 1.5 ± 0.2 (6 heads) 8.5 ± 0.8 (9 heads) |
| Clinical course, heads. (%) | | | |
| light | 4 (10.0) | 5 (12.5) | 5 (25.0) |
| heavy | 7 (17.5) | 2 (5.0) | 10 (50.0) |
| Died during the period of observation. heads (%) | 2 (5.0) | | 4 (20.0) |
| Were killed. heads. (%) | 6 (20.0) | 2 (5.0) | 2 (10.0) |
| Safety. heads. (%) | 32 (80.0) | 38 (95.0) | 14 (70.0) |
| Average daily growth of body weight. g (%) | 665.0 ± 39.0 (104.0) | 700.0 + 27.0 (109.4) | 640.0 ± 25.0 (100.0) |

TABLE 7

Comparative efficiency of the application of Irilis and well-known preparations for prophylactic treatment of gastrointestinal diseases of the new born calves, caused by "barn" micro flora

| Rates | Groups of calves | | |
|---|---|---|---|
| | First, heads = 35 Prophylaxis method Irilis | Second, heads = 35 Pectosorbin | Third, heads = 35 Immunoglobulin |
| Ill calves, heads. | 2 | 8 | 7 |
| Died of them, heads. | — | 5 | 3 |
| Diagnosis | Dyspepsia | Toxic dyspepsia | Toxic dyspepsia |
| Clinical course, heads.: | | | |
| light | — | 5 | 4 |
| heavy | 2 | 3 | 3 |
| Prophylactic efficiency, % | 94.3 | 77.1 | 80.0 |
| Safety, % | 100.0 | 80.0 | 91.4 |
| Average daily growth of body weight, g | 820.0 | 680.0 | 660.0 |

TABLE 8

Test results of the antibiotic preparations on broiler chickens

| Group | # house | N heads | Name | Dose | Term of taking, days | Results Term of growing, days | | | | | | | Aver. daily increment, g | Slaughter (46 days) Loss of cattle, % |
|---|---|---|---|---|---|---|---|---|---|---|---|---|---|---|
| | | | | Weight norm g/head | | 1 | 7 | 14 | 21 | 28 | 35 | 42 | | |
| 1 test | 46 | 30371 | VETOM | 75 mc/kg | 1) 1st 2) 4-13 | 39 g | 120 WEIGHT, % TO NORM 74.2 74.2 88.9 84.8 91.6 90.5 LOSS OF CATTLE, % TO NORM 0.4 0.4 0.5 0.56 1.32 0.8 | 310 | 590 | 950 | 1370 | 1805 | 42.0 37.9 | 4.19 |
| 2 test | 42 | 30660 | IRILIS | 4 mg/head | «>•) | 39 g | 81.7 WEIGHT, % TO NORM 77.1 80.8 82.9 86.0 87.0 LOSS OF CATTLE, % TO NORM 0.82 0.65 0.46 0.47 0.65 0.66 | | | | | | 37.6 | 3.96 |
| 3 test | 18-2 | 19642 | STF | 0.5 mg/head | «>•) | 39 g | 79.2 WEIGHT, % TO NORM 80.0 85.4 85.8 92.6 91.9 LOSS OF CATTLE, % TO NORM 0.79 0.67 0.64 0.8 0.8 0.76 | | | | | | 39.9 | 4.97 |
| 4 control | 50 | 30575 | ENTER-OSPORIN | 100 ml/5 000 heads | 4-5th | 39 g | 80.0 WEIGHT, % TO NORM 78.1 76.8 81.0 84.9 83.7 LOSS OF CATTLE, % TO NORM 0.45 0.7 0.54 0.46 0.66 0.7 | | | | | | 37.2 | 3.91 |

The invention claimed is:

1. A biopreparation for use in medicine and veterinary for prophylaxis and treatment of infectious diseases and dysbiosis of various etiology, containing an alive bacterial mass of strains *Bacillus subtilis* and *Bacillus licheniformis* and a protective medium, comprising: the strain *Bacillus subtilis* VKPM No. B-8611 of the strains *Bacillus subtilis* and *Bacillus licheniformis* VKPM No. B-8610 of the strains *Bacillus licheniformis*, in an efficient number.

2. The biopreparation according to claim 1 further comprising an excipient.

3. The biopreparation according to the claim 2 wherein the excipient contains protein, organic polymer, milk, serum, albumin, saccharose, lactose, calcium stearate, glucose, sodium bicarbonate, aluminum hydrate, methylcellulose, talc, cooking fat, paraffin, lanolin, cocoa butter, or aluminum hydroxide gel.

4. The biopreparation according to the claim 3 further comprising dextrans, polyglucin, starch, or polyvinyl pyrrolidone of organic polymers.

5. The biopreparation according to the claim 1 further comprising a solvent.

6. The biopreparation according to the claim 5 further comprising distilled water or boiled water, or a normal saline as the solvent.

7. The biopreparation according to claim 6 wherein the biopreparation is lyophilized.

8. The biopreparation according to claim 6 wherein the biopreparation is granulated.

9. The biopreparation according to claim 6 wherein the biopreparation is enclosed in a polymeric capsule.

10. The biopreparation according to claim 6 wherein the biopreparation is in a form of pills.

11. The biopreparation according to claim 6 wherein the biopreparation is in a form of suppositories.

12. The biopreparation according to claim 10 wherein the biopreparation is mixed with food ingredients.

13. A bacteria strain *Bacillus subtilis* VKPM No. B-8611 for manufacturing a biopreparation for prophylaxis and treatment of infectious diseases and dysbiosis of various etiology of human, animals and poultry.

14. A bacteria strain *Bacillus licheniformis* VKPM No. B-8610 for manufacturing a biopreparation for prophylaxis and treatment of infectious diseases and dysbiosis of various etiology of human, animals and poultry.

15. The biopreparation according to claim 1 wherein the biopreparation is lyophilized.

16. The biopreparation according to claim 1 wherein the biopreparation is granulated.

17. The biopreparation according to claim 1 wherein the biopreparation is enclosed in a polymeric capsule.

18. The biopreparation according to claim 1 wherein the biopreparation is in a form of pills.

19. The biopreparation according to claim 1 wherein the biopreparation is in a form of suppositories.

20. The biopreparation according to claim 1 wherein the biopreparation is mixed with food ingredients.

* * * * *

UNITED STATES PATENT AND TRADEMARK OFFICE
CERTIFICATE OF CORRECTION

| | | |
|---|---|---|
| PATENT NO. | : 8,414,878 B2 | Page 1 of 1 |
| APPLICATION NO. | : 11/919356 | |
| DATED | : April 9, 2013 | |
| INVENTOR(S) | : Irina Grigorievna Osipova et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 83 days.

Signed and Sealed this
Twenty-fourth Day of December, 2013

Margaret A. Focarino
*Commissioner for Patents of the United States Patent and Trademark Office*